United States Patent [19]

Arnold et al.

[11] Patent Number: 5,139,675
[45] Date of Patent: Aug. 18, 1992

[54] FILTRATION CLEANING SYSTEM

[76] Inventors: Edward R. Arnold, 151 Fairway La., Selmer, Tenn. 38375; H. Earl Ginn, 713 Summerwind Cir., Nashville, Tenn. 37215

[21] Appl. No.: 564,790

[22] Filed: Aug. 8, 1990

[51] Int. Cl.⁵ .................... B01D 35/06; B01D 61/26
[52] U.S. Cl. .................... 210/636; 210/646; 210/748; 210/797; 210/243; 210/257.1; 210/257.2; 210/409; 134/1; 204/149; 204/186; 422/22
[58] Field of Search ........... 210/636, 645, 646, 695, 210/748, 791, 222, 223, 243, 257.2, 407, 409, 257.1, 797; 134/1; 204/149, 186; 422/22; 604/4, 5, 6

[56] References Cited

U.S. PATENT DOCUMENTS

| | | | |
|---|---|---|---|
| 1,773,275 | 8/1930 | Neeley | 210/223 |
| 2,596,743 | 5/1952 | Vermeiren | 210/222 |
| 3,511,776 | 5/1970 | Avampato | 210/695 |
| 3,625,884 | 12/1971 | Waltrip | 210/152 |
| 4,288,323 | 9/1981 | Brigante | 210/222 |
| 4,365,975 | 12/1982 | Williams et al. | 48/197 R |
| 4,367,143 | 1/1983 | Carpenter | 210/222 |
| 4,407,719 | 10/1983 | Van Gorp | 210/695 |
| 4,473,449 | 9/1984 | Michaels et al. | 210/748 |
| 4,545,887 | 10/1985 | Arneson et al. | 204/280 |
| 4,582,629 | 4/1986 | Wolf | 210/748 |
| 4,659,479 | 4/1987 | Stickler et al. | 210/695 |
| 4,746,425 | 5/1988 | Stickler et al. | 210/695 |
| 4,865,747 | 9/1989 | Larson et al. | 210/695 |
| 4,865,748 | 9/1989 | Morse | 210/748 |
| 4,888,113 | 12/1989 | Holcomb | 210/222 |

FOREIGN PATENT DOCUMENTS 463844 8/1928 Fed. Rep. of Germany .
417501 9/1934 United Kingdom .

OTHER PUBLICATIONS

Aquabel, Brochure—date unknown.
The Ion Stick, Brochure, York Energy Conservation—date unknown.

Primary Examiner—W. Gary Jones

[57] ABSTRACT

A dialyzer reprocessing device and method are disclosed. The device and method are of the type which include a dialyzer and means for cleaning the dialyzer by treatment with fluids. Included is a treating device for modifying the fluids prior to introduction into the dialyzer. The treating device includes means for directly injecting into the fluids electromagnetic radiation having a preselected frequency through a nonelectrically insulated conductor.

16 Claims, 3 Drawing Sheets

FILTRATION CLEANING SYSTEM

FIELD OF THE INVENTION

This invention relates generally to filtration and membrane technology and, in particular, to enhancing the lifetime of utility of filtration devices.

BACKGROUND OF THE INVENTION

Many industrial and scientific operations today depend upon filtration to separate valuable, nutrient or metabolic substances from waste or otherwise unusable products. These operations include direct osmosis, reverse osmosis and ultrafiltration methods; all involve passage of fluids over semipermeable membranes which allow the fluid to be separated from small dissolved molecules colloids, and suspended solids. Membrane-retained components are collectively called the concentrate or retentate. Materials permeating the membrane are called the filtrate or permeate.

Direct or natural osmosis utilizes a semipermeable membrane flanked on one side by a concentrated solute solution and on the other by a less concentrated solution. Osmotic forces will tend to equalize the solute concentration by passing water or other solvent through the membrane, while the solute cannot permeate the membrane. In reverse osmosis, application of pressure to the concentrated solution will force pure water or solvent back through the membrane, thereby concentrating the solute. In ultrafiltration, on the other hand, pressure is applied to a solution to force the solvent through the semipermeable membrane. That is, ultrafiltration is pressure-driven osmotic filtration on a molecular scale.

In addition to purely osmotic membranes which involve passage of solvent in one direction or the other, dialyzing membranes permit small solute molecules and ions to permeate the membranes. Dialysis basically is a membrane transport system in which solute molecules are exchanged between two liquids. For example, globular proteins in solution can easily be separated from low-molecular weight solutes utilizing a semipermeable membrane to retain protein molecules yet allow small solute molecules and water to pass through.

The largest contemporary use of dialysis is in hemodialysis, the treatment of the blood of persons with end-stage renal disease in which the kidneys are no longer capable of removing products of metabolism from the blood and excreting them. Hemodialyzers or "artificial kidneys" have now been used for almost 40 years to treat patient with severe renal failure. Many thousand persons with permanent renal failure or even total kidney removal are maintained in health for years at a time, their lives depending entirely on the artificial kidney.

In an artificial kidney, blood flows continually between membrane surfaces (the blood compartment); on the other side of the membrane is the dialyzing fluid (the dialysate compartment). The membrane is porous enough to allow all constituents of the plasma except plasma proteins to diffuse freely in both directions— from plasma into the dialyzing fluid and from the dialyzing fluid back into the plasma. If the concentration of a substance is greater in the plasma than in the dialyzing fluid, there will be a net transfer of the substance from the plasma into the dialyzing fluid. The amount of the substance that transfers depends on: (1) the difference between the concentrations on the two sides of the membrane; (2) molecular size, the smaller molecules diffusing more rapidly than larger ones; and (3) the length of time that the blood and fluid remain in contact with the membrane.

Types of dialyzers include: (1) coil, which incorporates a membrane in the form of a flattened tube wound around a central, rigid cylinder core, with a supporting mesh between adjacent portions of the membranes; (2) parallel plate, which incorporates a membrane in tubular or sheet form supported by plates in a sandwiched configuration; and (3) hollow-fiber, which incorporates the membrane in the form of very small fibers having a microscopic channel running through them. Most sheet and hollow-fiber membranes are cellulosic, although other materials have also been prepared and evaluated.

Probably the most important technical innovation in dialysis technology in support of hemodialysis is the development of hollow-fiber dialysis membranes and devices. One known dialyzer configuration is a capillary flow dialyzer, comprised of multiple hollow-fiber membranes contained within a housing. The hollow-fiber membranes are cylindrical capillaries having a diameter of less than 1 $\mu$m, and whose walls function as the semipermeable membrane, permitting selective exchange of materials across the walls.

Since 1980, the reuse of hemodialyzers has risen dramatically. In 1986, the Association for the Advancement of Medical Instrumentation (AAMI) issued guidelines for the recommended practice in the reuse of hemodialyzers (Association for the Advancement of Medical Instrumentation, "Reuse of Hemodialyzers," Arlington, Va., 1986), stating that safe multiple use of hemodialyzers may actually improve the quality of care and/or access to dialysis. In large measure, the acceptability of reuse has also depended on the development and use of hollow-fiber hemodialyzers, which can be reprocessed to be equivalent in function, cleanliness, and sterility to a new hollow-fiber hemodialyzer.

Reprocessing of hemodialyzers after patient dialysis depends ultimately on cleaning and disinfecting of the dialyzer. Each piece of equipment used for reprocessing must be appropriately designed, constructed and validated to perform its intended task. Types of reprocessing system vary from sophisticated microprocessor-controlled systems to hand-operated valving systems. In reprocessing, both the blood compartment and the dialysate compartment are flushed with cleaning agents, such as hydrogen peroxide or sodium hypochlorite, and rinsed with water. The water is filtered through a nominal 5 $\mu$m (micron) filter and should have a bacterial colony count of less than 200 /ml and/or a bacterial lippolysaccharide concentration of less than 1 ng/ml as measured by the Limulus amebocyte lysate assay. The dialyzer should also be free of any visible clotted blood.

The rinsed and cleaned dialyzer must also be treated by a process that prevents adverse effects due to microbial contamination. Typically, the blood compartment of the dialyzer is sterilized or subjected to high level disinfection. In practice, the dialysate compartment is also subjected to the same process because germicides pass through the membrane of the device. Typically, formaldehyde is used as the germicide, although other chemical germicides may be used which are shown not to damage the integrity of the dialyzer and must rinse out of the dialyzer to below known toxic levels with a rinse-out period established for the particular germicide. Care must also be taken not to mix reactive materials such as sodium hypochlorite and formaldehyde.

Hemodialyzers, reprocessed in conformance with the AAMI specific guidelines and performance tests, have an average use number, i.e., the number of times a particular hemodialyzer has been used in patient dialysis treatment may be about 8-15. Considering that hemodialyzers are used at least three times per week per patient, it would be highly desirable to improve the reprocessing system to increase the use number of a hemodialyzer.

Treatment of water to improve its properties for a variety of industrial and residential applications has been widely discussed in the scientific literature and in patents issued in the United States and other countries. The variety of devices for such treatment is so great that a comprehensive review thereof will not be undertaken here, it being generally known that such systems have been proposed based on technologies including static and dynamic magnetic treatment, treatment using electrostatic fields, ultrasound, externally-generated heating radiation (such as microwave), directly injected electromagnetic radiation, and, of course, a variety of chemical treatment techniques.

The scientific basis for the effects of various water treatment techniques has been widely debated and discussed, and opinions in the scientific community vary dramatically about the potential for such treatment techniques on an industrial or commercial scale. For example, in the Soviet Union, magnetic treatment of water to assist in removal or prevention of scale has been reported. Favorable analysis of such treatment has been criticized by literature generated in the United States. Some of the theories discussed include one which advocates the hypothesis that magnetic treatment decreases the surface tension of the water molecules, thereby making the treated water "wetter" than untreated water. Another advocates the belief that the magnetic fields generated within the water act only on the impurities contained within the water. Others related to ionic charge theory, minor changes in pH, changes in the zeta potential or the like.

Despite such debate over the scientific basis of the treatment effect, a number of individuals and companies are continuing to suggest new types of treatment devices for previously discussed applications and new technologies for unrelated and surprisingly diverse applications.

Examples of magnetic water treatment devices include the following:

Stickler et al., U.S. Pat. No. 4,746,425 issued May 24, 1988 for "Cooling System for Magnetic Water Treating Device" and Stickler, et al., U.S. Pat. No. 4,659,479 issued Apr. 21, 1987 for "Electromagnetic Water Treating Device", both use a pipe core of alternating magnetic and non-magnetic sections with an electromagnet surrounding the pipe through which the fluid to be treated passes.

Another treatment system is disclosed in Larson, et al., U.S. Pat. No. 4,865,747, issued Sep. 12, 1989, for "Electromagnetic Fluid Treating Device and Method". An electromagnetic field having a voltage which operates in the range of 1 kHz to 1000 MHz is applied to a non-ferromagnetic conduit in which a ferromagnetic core is mounted. The core acts as a sacrificial anode and as a receiving antenna for the radiofrequency electromagnetic radiation.

A permanent magnet system is described in Mitchell, U.S. Pat. No. 4,808,306 issued Feb. 38, 1989 for "Apparatus for Magnetically Treating Fluids". A field generator is mounted on one side of a pipe, through which fluid to be treated passes, in a non-ferromagnetic housing. A magnet is embedded in the housing and has an odd number of sections of alternating polarity. For fuel treatment, the uppermost section is desirably a south polar magnetic field. If water is to be treated, a north ferromagnetic plate mounted adjacent to but outwardly from the pipe is used for increasing magnetic field strength. Mitchell indicates that his device can lead to fuel consumption savings, to maintain minerals and other contaminates of water in solution (softening of water), prevention of scale and rust and to improve the taste, cleaning and solvent properties of water.

Additional patents which refer to the use of magnets to treat water include Carpenter, U.S. Pat. No. 4,367,143 issued Jan. 4, 1983, for "Apparatus for Magnetically Treating Liquid Flowing Through a Pipe and Clamping Means Therefor". This patent discusses applying a plurality of strips of ferromagnetic material contained in a shoe member on the outside of a pipe, the number of magnetic strips and the power of the magnets being selected for a particular pipe size. The polarities of the magnets in each strip are aligned in the same way, e.g., all south polar ends being oriented upstream with respect to water flow. See, also, Kulish, U.S. Pat. No. 4,605,498 issued Aug. 12, 1986 for "Apparatus for Magnetic Treatment of Liquids". The magnet arrangement of this patent (surrounding arcuate shape magnets) is such that the south pole magnetic fields are concentrated toward the axis of a pipe through which liquids to be treated pass, while the north poles are directed radially outwardly.

A unique magnet arrangement for water treatment is disclosed in U.S. Pat. No. 4,888,113 issued to Holcomb on Dec. 19, 1989 for "Magnetic Water Treatment Device". In this patent, Holcomb discusses the use of a plurality of rectangular magnets attached to the exterior of a pipe. The magnets are arranged in pairs adjacent the pipe such that the positive pole of one pair is oriented to one end of a support housing and the negative pole is oriented toward the other end of the housing. Another similarly constructed housing is secured to the opposite side of the pipe, the second housing also from those in the first housing. Thus the positive pole of the first set faces the negative pole of the second set to cause an "attractive" mode of magnetic flux treatment. Applications such as scale prevention, as well as use in washing machines, swimming pools, ice rinks, livestock watering, and coffee brewing are suggested. The patent also suggests that the taste of treated water is superior to that of untreated water. The patent further mentions that the magnetic force fields can be generated through wound iron coils coupled to a DC generator.

Another water treatment technique is that disclosed in U.S. Pat. No. 4,865,748 issued Sep. 12, 1989 to D. Morse and entitled "Method and System for Variable Frequency Electromagnetic Water Treatment". In this device, a non-insulated conductor in direct contact with a fluid to be treated is coupled to a generator of electromagnetic radiation, preferably in the radio frequency range. According to the patent, the radiation is injected at a frequency which is related to the electromagnetic radiation absorption or emission profile of the particular system being treated. This patent also focuses on the use of that system for the elimination and prevention of scale build-up in boiler systems and the like.

These patents are representative of the wide diversity of treatment techniques discussed in the art and it is important for a more complete understanding of the prior art to read the "Background" sections of each of the foregoing patents. Also the tabular listings of art cited against such patents should be reviewed. Each of the background disclosures and listings is incorporated herein and is made available by the copies of the patents supplied herewith.

SUMMARY OF THE INVENTION

According to the present invention, reuse or lifetime of utility of a filtration device is enhanced by treatment involving electromagnetic treatment of the feed fluids to the device. The present invention provides electromagnetic treatment for fluids to be received by a filter in a filtration device, which includes a conduit for conveying the fluids to the filter and an outlet conduit through which the fluids are discharged, by directly injecting into the fluids electromagnetic radiation at a preselected frequency through a non-electrically insulated conductor.

In an illustrated embodiment, reuse of hemodialyzers is enhanced by employing a treating device for modifying the reprocessing fluids in a dialyzer reprocessing device prior to their introduction into the dialyzer; the treating device includes an electromagnetic treatment device for directly injecting into the fluids electromagnetic radiation having a preselected frequency through a non-electrically insulated conductor. The electromagnetic treatment device includes an electromagnetic frequency generator for generating an electromagnetic signal having electric and magnetic components electrically coupled with at least one non-electrically insulated conductive probe which is in contact with the fluids. Preferably, the treating device includes a pair of conductive probes spaced apart from one another within a conduit for conveying the fluids to the dialyzer.

According to another aspect of the invention, methods for enhancing lifetime of a filtration device and reuse of a dialyzer are provided. Other ways in which the present invention provides improvement to this art will become apparent from the following description, taken in conjunction with the drawings which accompany it.

BRIEF DESCRIPTION OF THE DRAWINGS

The accompanying drawings, which are incorporated in and constitute a part of the specification, illustrate the preferred embodiments of the invention and, together with the general description give above and the detailed description of the preferred embodiments given below, serve to explain the principles of the invention. Like reference numerals are used to describe like components, and in which.

DETAILED DESCRIPTION OF PREFERRED EMBODIMENTS

In the description of the preferred embodiments of the invention a dialyzer reprocessing system will be used as an example, but it should be appreciated at the outset that the principles of the present invention have a much wider application, that is, in any process using filtration devices in which the lifetime of use of the filter means is of concern, e.g., separation of whey liquid from whey in cheese making. Also, many of the components of the preferred embodiment are shown in only general form, because the present invention can be employed with or as additions to numerous types of cleaning or filtering systems. Accordingly, such features of available systems as power controls, feed fluid reservoirs and pumps, auto fill systems, timers, temperature settings, alarms, and the like, are not shown.

Figure 1:
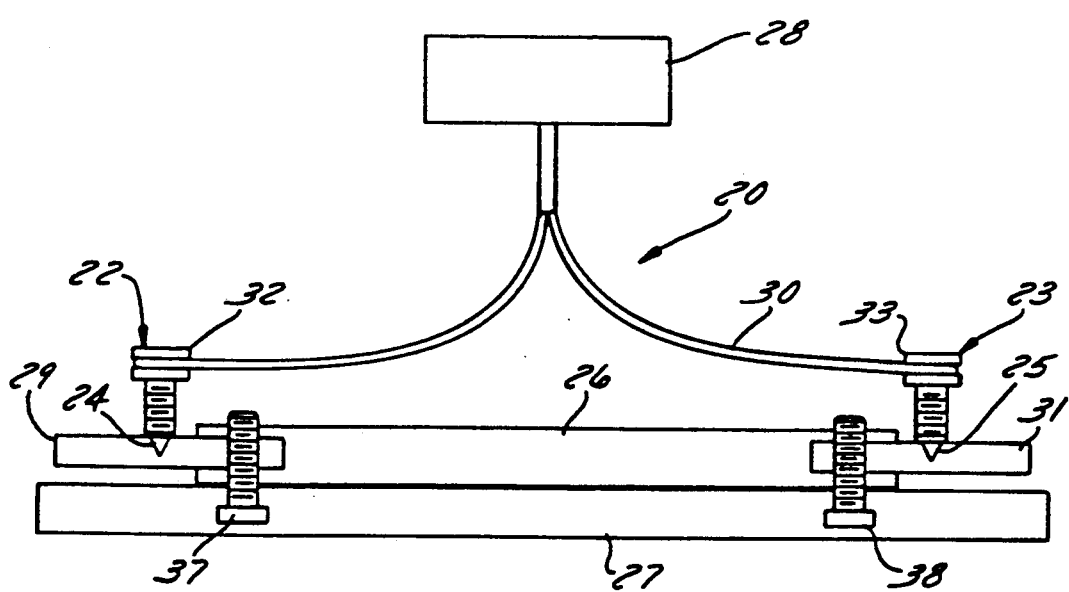
FIG. 1 is a side sectional schematic view of the treating device in accordance with the present invention.

Reference is initially made to FIG. 1 depicting a treating device 20 according to the present invention. Treating device 20 includes at least one conductive probe 22, and preferably a second probe 23, spaced apart from probe 22, typically about 5.5 in. apart. Probes 22 and 23 are mounted such a way that the tips 24 and 25 of the probes 22 and 23 are in direct contact with fluids that flow through a conduit 26. The probe is mounted in the conduit so that water is treated while flowing through conduit prior to entry into the filter or dialyzer to be cleaned or reprocessed. An electromagnetic wave generator 28 is coupled to a coaxial wire 30 which is in turn connected to the external connectors 32 and 33 of the probes 22 and 23, respectively, so that electromagnetic radiation consisting of magnetic and electrical wave components is provided to tips 24 and 25. The two probe arrangement serves to direct or focus the electric and magnetic fields of the electromagnetic radiation. Conduit 26 where probes 22 and 23 are located is secured to, for example, a wooden dowel 27 to maintain linearity of the conduit. Connectors 29 and 31 are suitably polypropylene tee-type connectors or other suitable autoclavable material.

The probe is suitably constructed of a non-corrosive material, such as stainless steel, platinum or other conductive materials. The coaxial wire 30 is conventional. Conduit 26 is typically a silastic tubing. Probes 22 and 23 can be cut into the tubing and secured with ties or clamps 37 and 38. Ties 37 and 38 are conventional.

In a preferred embodiment, the generator 28 employed for the direct injection of electromagnetic radiation operates at about 40 volts (peak to peak) with 425 milliamps current. The frequency of the radiation generated is in the range of 1 kHz to 1000 MHz. It has been found that a frequency, preferably, in the range of about 20 to 60 MHz is useful in treating water and aqueous solutions. The length of time for injection of the electromagnetic radiation can be varied widely, as can the location of the probes. As explained below, the probes in a hemodialyzer reprocessing system are preferably located where all fluids entering the dialyzer will undergo electromagnetic treatment.

Figure 2:
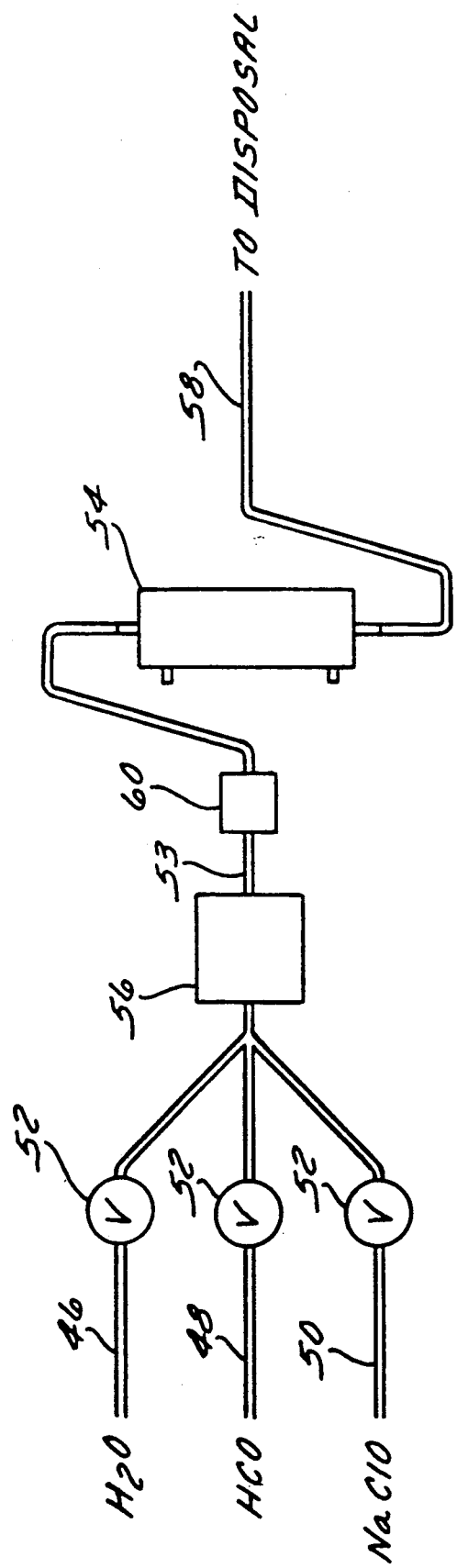
FIG. 2 is a schematic flow diagram of a dialyzer reprocessing system including electromagnetic treatment in accordance with the present invention.

Reference is made to FIG. 2 where a schematic diagram or a dialyzer reprocessing system is shown. Inlets 46, 48, and 50 are provided for sodium hypochlorite solution (bleach), formaldehyde, and bacteriological standard water, respectively. Typically, the cleaning agent is about 15% sodium hypochlorite, although 8-10% hydrogen peroxide may also be used. The formaldehyde used as the disinfecting agent is generally about 1-2%. The water is used as a rinse and as a diluent for the stock cleaning and disinfecting solutions. Each fluid line is provided with valves 52 so that the fluids may be selectively introduced into a dialyzer 54 to be cleaned and processed. The fluids are pumped to the dialyzer 54 via an ultrafiltration pump 56. Prior to entry into dialyzer 54, the fluids enter treating device 60 in which the conductive probes are located in the conduit 53 leading to the dialyzer, as explained above. Disposal of the fluids is via conduit 58.

Figure 3:
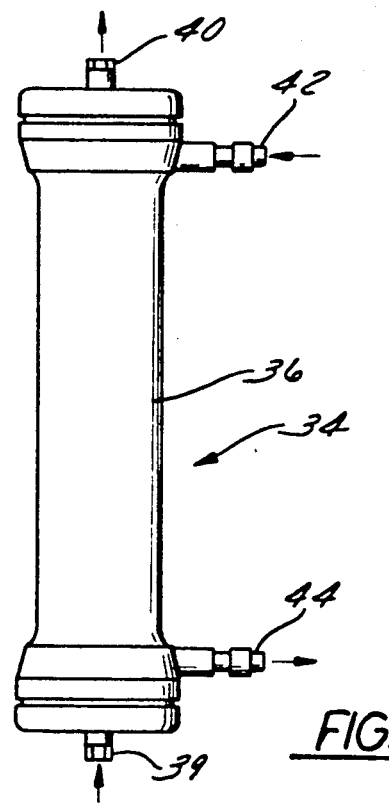
FIG. 3 is a side plan view of a hemodialyzer of the hollow-fiber type.

As best seen in FIG. 3, a hemodialyzer 34 of the hollow-fiber type is typically a cylindrical unit 36 in which reside the fibers (not shown) with a blood inlet 38 and outlet 40, and a dialysate inlet 42 and outlet 44.

Figure 4:
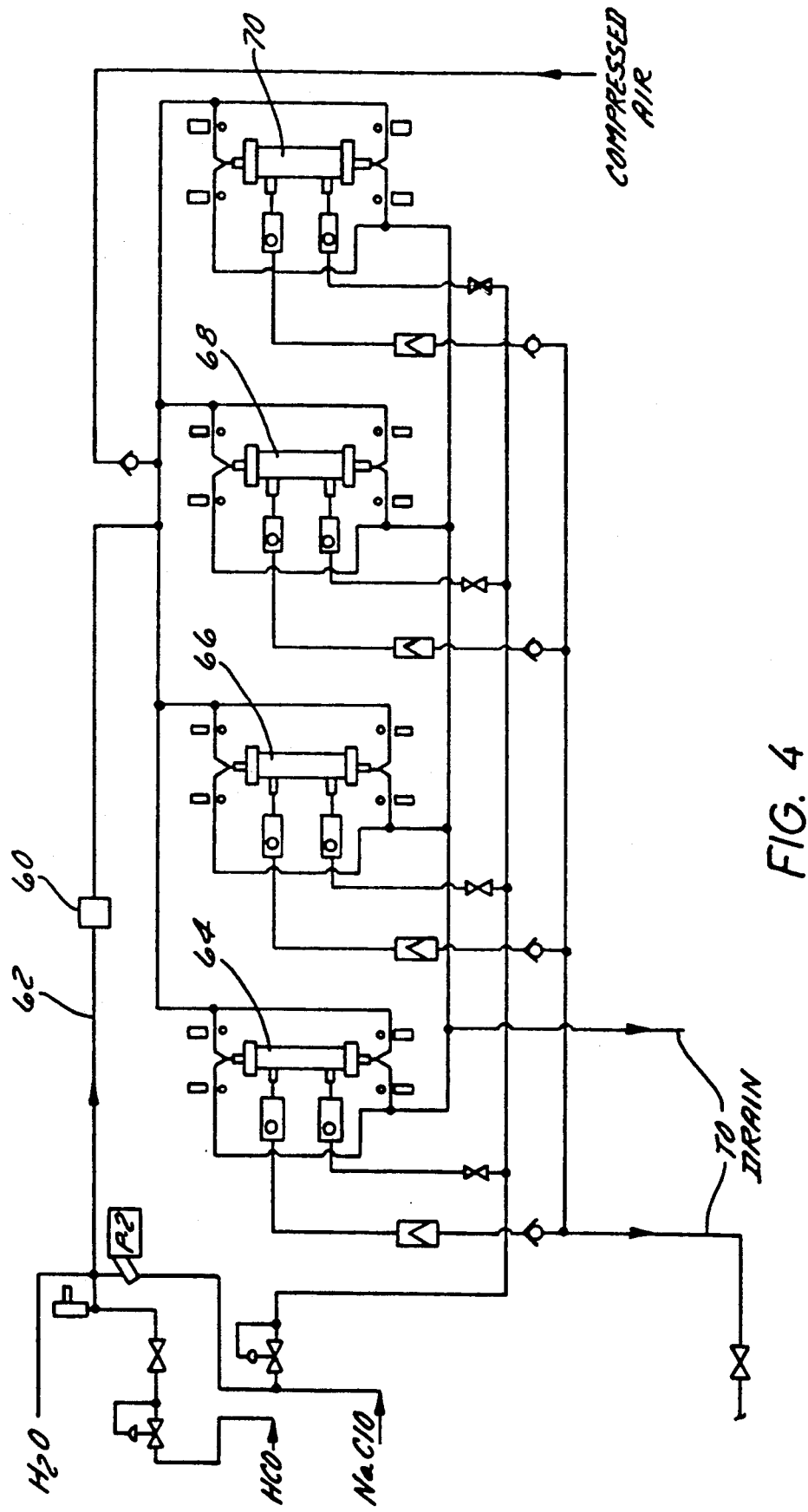
FIG. 4 is a schematic flow diagram of a dialyzer reprocessing system including electromagnetic treatment in which multiple dialyzers are simultaneously reprocessed.

FIG. 4 is a schematic diagram of a dialyzer reprocessing system in which up to four dialyzers 64, 66, 68 and 70 of the type shown in FIG. 3 may simultaneously be cleaned and processed. Treating device 60 is shown in conduit 62 through which all fluids enter to all four dialyzers.

Experiments have been performed in which the fluids used in dialyzer reprocessing were subjected to electromagnetic radiation in accordance with the present invention and the use number of the dialyzers determined. Dialyzers reprocessed with the conventional cleaning and disinfecting procedures were compared with dialyzers in which the reprocessing included electromagnetic treatment of the cleaning, rinsing and disinfecting fluids in accordance with the present invention.

The comparative testing was performed over a ten-month period from Sep. 1, 1989 to Jun. 30, 1990. The dialyzers used were Hemaflow F60 and Hemaflow F80, both manufactured by Fresenuis AG, Oberursel, West Germany, and Clirans TAF 175, manufactured by Terumo Corporation, Tokyo, Japan, for both the controls and treated dialyzers.

The electromagnetic treatment device in accordance with the present invention was installed into the cleaning circuit fluid line on Feb. 27, 1990. The control filters were all filters that had starting and ending dates of use prior to Feb. 27, 1990. The treated filters were all filters with start and stop dates after Feb. 27, 1990. Any dialyzer which exhibits a loss of 10% in any performance test as specified by the AAMI guidelines may not be reused. The dialyzer reuse data are present in Table 1.

Table 1

| | Dialyzer Reuse* | | | | | |
|---|---|---|---|---|---|---|
| | Control Start and Stop Dates of Use Before 2/27/90 | | | Treated** Start and Stop Dates of Use After 2/27/90 | | |
| | F60 | F80 | TAF 175 | F60 | F80 | TAF 175 |
| No. of Filters | 27 | 17 | 24 | 33 | 14 | 13 |
| Minimum | 26 | 4 | 2 | 5 | 5 | 2 |
| Maximum | 34 | 16 | 19 | 57 | 35 | 35 |
| Mean | 19.37 | 7.83 | 8.96 | 23.73 | 13.29 | 18.77 |
| Standard Deviation | 7.75 | 2.96 | 5.58 | 11.88 | 7.29 | 9.35 |
| Increase Percentage | | | | 22.5% | 69.7% | 109.5% |

*All filters that started before 2/27/90 and extended beyond 2/27/90 were excluded from this summary.
**Active filters included in this category.

The following conclusions were consistent for the three filter types utilized:

1) No difference was found for reuse minimum when the two time categories (before vs. after) were compared.

2) Reuse maximum values for the after categories were larger than the before category.

3) Average reuse was increased by electromagnetic fluid treatment.

The percentage increases for the filters were 22.5% for the F60, 69.7% for the F80, and 109.5% for the TAF 175.

In any system which involves interaction of a membrane with fluids and transport of substances across the membrane, the lifetime of utility of the filtration device is dependent upon many variables, such as the membrane material, the feed fluids used, and general operating conditions. These factors ultimately affect the structural integrity and performance of the membrane. Studies comparing dialyzers reprocessed in accordance with the present invention and those subjected to conventional cleaning demonstrate dramatically improved lifetimes for the dialyzers. In fact, any system involving filtering or cleaning of a filtration device is benefitted by fluid treatment in accordance with the present invention to increase lifetime utility of the device.

While the present invention has now been disclosed with reference to certain preferred embodiments and exemplified with regard thereto, those skilled in the art will appreciate the various substitutions, modifications, omissions and changes that may be made without departing from the spirit thereof. Accordingly, it is intended that the scope of the present invention be limited solely by the broadest interpretation accorded the appended claims.

We claim:

1. In a dialyzer reprocessing device of the type which includes a dialyzer and means for cleaning the dialyzer by treatment with fluids, and a conduit for conveying the fluids to the dialyzer, the improvement comprising a treating device for modifying the fluids prior to introduction thereof into said dialyzer, said treating device comprising means for directly injecting into said fluids electromagnetic radiation having a preselected frequency through a non-electrically insulated conductor.

2. The device of claim 1, wherein said conductor is located within said conduit.

3. The device of claim 2, wherein said treating device includes a pair of conductors spaced apart from one another within said conduit.

4. The device of claim 1, further including a fluid reservoir and wherein said conductor is located in said reservoir.

5. The device of claim 1, wherein said frequency is in the range of about 1 kHz to about 1000 MHz.

6. The device of claim 5, wherein said frequency is in the range of about 20 to about 60 MHz.

7. The device of claim 1, wherein said treating device includes an electromagnetic frequency generator coupled to the conductor.

8. The device of claim 7, wherein said conductor is constructed of stainless steel.

9. A dialyzer reprocessing device, comprising:
   a dialyzer;
   conduit means for conveying cleaning, rinsing and disinfecting fluids to said dialyzer;
   said dialyzer arranged to receive said fluids and having an outlet conduit through which said fluids are discharged; and
   treatment means for treating said fluids to be received by said dialyzer through said conduit means by directly injecting into said fluids electromagnetic radiation having a preselected frequency through a non-electrically insulated conductor.

10. An apparatus for reprocessing or otherwise cleaning filtering systems, comprising:
   filter means containing at least one filtration membrane module, said filter means including inlet means, first outlet means for concentrate and second outlet means for permeate;
   cleaning means for said filter means including means for delivering cleaning fluids under pressure to said inlet means of said filter means; said cleaning means including a first conduit interconnecting said delivery means and said first outlet means and a valve means for selectively directing said fluids from said delivery means to said inlet means or to said first outlet means through said first conduit means; and
   electromagnetic treatment means for directly injecting into said fluids through said first conduit means electromagnetic radiation of a preselected frequency through a non-electrically insulated conductor.

11. A method for enhancing the lifetime of filters in a system in which fluids are fed into filters, comprising the steps of:
   (a) providing a filter system, a supply of fluids and conduit means for conveying the fluids to the filters;
   (b) generating an electromagnetic signal at a preselected frequency;
   (c) injecting said electromagnetic signal into said fluids at a location prior to their entering the filter system, through a nonelectrically insulated conductor in electrical contact with the fluids; and
   (d) said preselected frequency is selected from the range of 20 to 60 MHz.

12. A method of extending the reuse of dialyzers, comprising the steps of:
   (a) providing one or more dialyzers to be reprocessed for reuse arranged to receive cleaning and disinfecting fluids;
   (b) subjecting said dialyzers to said cleaning fluids;
   (c) generating an electromagnetic signal at a preselected frequency;
   (d) injecting said electromagnetic signal into said fluids at a location prior to their entering a filter, through a conductor in electrical contact with the fluids; and
   (e) said preselected frequency is selected from the range of 20 to 60 MHz.

13. A filtration device, comprising:
   a filter;
   conduit means for conveying feed fluids to a filter;
   said filter being arranged to received said fluids and having an outlet through which said fluids are discharged; and
   treatment means for treating said fluids to be received by said filter by directly injecting into said fluids electromagnetic radiation having a preselected frequency through a non-electrically insulated conductor.

14. The device of claim 13, wherein said frequency is in the range of about 20 to about 60 MHz.

15. The device of claim 13, wherein said treatment means includes an electromagnetic frequency generator coupled with at least one non-electrically insulated conductor in contact with said fluids.

16. The device of claim 15, wherein said treating device includes a pair of conductors spaced apart from one another and located within said conduit means.

* * * * *